United States Patent [19]

Schadenberg

[11] 4,102,797
[45] Jul. 25, 1978

[54] COMPOUNDS CONTAINING BOTH UREA AND URETHANE GROUPS

[75] Inventor: Hendrik Schadenberg, Amsterdam, Netherlands

[73] Assignee: Shell Oil Company, Houston, Tex.

[21] Appl. No.: 682,539

[22] Filed: May 3, 1976

[51] Int. Cl.$^2$ .............................................. C07C 127/19
[52] U.S. Cl. .................... 252/51.5 A; 260/332.2 R;
560/24; 560/27; 560/28; 560/32; 560/133;
560/137; 560/159
[58] Field of Search ........... 260/471 C, 482 C, 468 E;
252/51.5 A; 560/27, 133, 137, 115, 159

[56] References Cited

U.S. PATENT DOCUMENTS

| 3,684,771 | 8/1972 | Braun ........................... 260/482 C X |
| 3,746,742 | 7/1973 | Schuierer et al. ............... 260/471 C |
| 3,766,070 | 10/1973 | Wulfers ........................... 252/51.5 A |
| 3,783,152 | 1/1974 | Larsen ............................. 260/471 C |
| 4,013,450 | 3/1977 | Olin et al. ..................... 260/471 C X |

FOREIGN PATENT DOCUMENTS 468,911  11/1975  U.S.S.R.

Primary Examiner—Richard L. Raymond
Attorney, Agent, or Firm—Ronald R. Reper

[57] ABSTRACT

Novel compounds of the general formula:

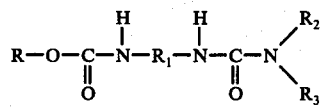

wherein R and $R_2$ are hydrocarbyl groups, $R_1$ is a hydrocarbylene group and $R_3$ is hydrogen or a hydrocarbyl group, which groups R, $R_1$, $R_2$ and $R_3$ may be substituted by or contain one or more heteroatoms or heterogroups, have utility as antioxidants for organic materials such as lubricating oils.

8 Claims, No Drawings

COMPOUNDS CONTAINING BOTH UREA AND URETHANE GROUPS

The invention is concerned with novel compounds and with organic compositions containing such compounds which have improved stability against oxidation.

The Applicant has discovered a new class of compounds, comprising both a urea and a urethane group, which improve the oxidation stability of organic materials.

According to this aspect of the invention, a composition comprises a major proportion of an organic material and a minor proportion of a compound of general formula:

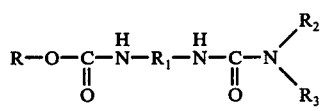

wherein R and $R_2$ are hydrocarbyl groups, $R_1$ is a hydrocarbylene group and $R_3$ is H or a hydrocarbyl group, which groups may be substituted or interrupted by one or more heteroatoms or heterogroups.

This new class of compounds may be used to stabilize a wide range of different types of organic material. For example, the compounds may be used to stabilize crude mineral oil; lubricating oil; fuels, e.g. heavy residual fuels and distillate fuels such as gasoline, aviation turbine fuel and gas oil; functional oils e.g. hydraulic oils, heat transfer oils and automatic transmission fluids; greases; plastics e.g. polypropylene and polyethylene and rubbers e.g. natural or synthetic rubbers. The organic material is suitably hydrocarbonaceous and is suitable derived from natural sources e.g. crude mineral oil. The organic material may also be a synthetic material, e.g. esters or hydrocarbons, which may be used, for example, as lubricating oils.

Most suitably the organic material is a lubricating oil and particularly suitable mineral oils are high and very high viscosity index lubricating oils. Preferably such oils are mineral oils and may be of a naphthenic, paraffinic or mixed naphthenic/paraffinic nature, depending on the crude oil from which they are prepared. They may be obtained by straight distillation of oils, which after distillation, have been subjected to one or more refining treatments, such as an extraction, dewaxing or hydrogenation treatment. Such oils may also contain residual components. It is already known to add certain compounds to such oils to improve the oxidation stability thereof, but most compound that have been proposed for this purpose show a strongly decreasing antioxidant activity at increasing temperatures. This is a disadvantage of such compounds when the oils are exposed to relatively high temperatures, for example when they are used as lubricating oils in combustion engines. Moreover, there is also a tendency towards increasing thermal engine load, as a result of which increasing demands are being made on the oxidation stability of lubricating oils. It has been found that the compounds of the present invention are particularly suitable for stabilizing these oils against oxidation at elevated temperatures.

Each hydrocarbyl group, which may be the same or different, of the compounds of general formula I, may be an alkyl group, a cycloalkyl group, an aryl group, an alkaryl group, an aralkyl group and the hydrocarbylene group is a corresponding divalent group. The alkyl groups may be unsaturated. The groups may be interrupted by one or more heteroatoms, i.e. the group may be a heterocyclic group, or may be substituted by one or more hetero groups e.g. halogen atoms, especially chlorine atoms; sulphur atoms; nitrogen atoms; alkoxy groups; ester groups; polyether groups; carbonyl groups; amino groups; and hydroxyl groups. Chlorine, hydroxyl and amine substituents are particularly useful substituents.

Suitably the R group, of the compounds of general formula I, is (a) An alkyl group e.g. a $C_1$ to $C_{30}$ alkyl group, more preferably a $C_8$ to $C_{16}$ alkyl group such as a $C_{12}$ alkyl group.

(b) A group which is bound directly to the urethane group by means of a carbon atom of an aromatic ring e.g. an aryl or alkarryl group e.g. phenyl, alkphenyl, naphthyl, alknaphthyl, biphenyl, alkbiphenyl, aralkaryl or alkaralkaryl group. The alkaryl group may comprise 1 or 2 aromatic rings which may be fused or non-fused and preferably comprises from 1 to 6 alkyl groups, such as $C_1$ to $C_{20}$, preferably $C_1$ to $C_6$, alkyl groups, which may be primary, secondary or tertiaryalkyl groups e.g. methyl, ethyl, propyl, secondarypropyl, butyl, secondary butyl or tertiary butyl groups. One preferred type of alkaryl groups are alkphenyl groups comprising from 1 to 3 alkyl groups and wherein at least one alkyl group is a tertiaryalkyl group, e.g. a tertiarybutyl group, which is preferably in the ortho-position relative to the urethane group. Another preferred type of alkaryl groups are hydroxy-substituted aralkyl or alkaralkaryl groups of the formula

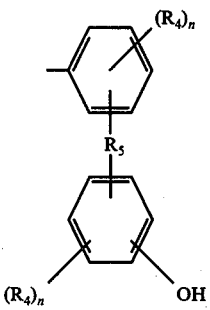

wherein the $R_4$ groups, which may be the same or different groups, are $C_1$ to $C_{20}$, preferably $C_1$ to $C_6$, alkyl groups of the type discussed above, $R_5$ is a $C_1$ to $C_6$ alkylene group and $n$ is 0,1 or 2. Preferably, the alkaralkaryl group is substituted in both ortho-positions relative to the urethane group by an alkyl group and the alkylene group. Preferably, such alkyl groups are tertiaryalkyl groups and preferably the alkylene group is a methylene group. Preferred tertiaryalkyl groups are teriarybutyl groups. Preferably, the hydroxyl group is also substituted in both ortho-positions by such an alkyl group and the alkylene group. Preferably, the hydroxy-substituted aralkaryl group has the formula

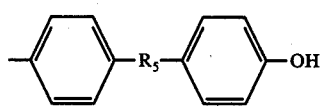

wherein $R_5$ is as described above.

Preferred aryl groups are phenyl and halophenyl groups e.g. a 4-chlorophenyl group, with the latter being particularly preferred.

(c) A group which contains at least one aromatic ring and is bound directly to the urethane group by means of an aliphatic carbon atom of the group e.g. aralkyl groups, such as benzyl, alkbenzyl, phenethyl and alkphenethyl groups with alkbenzyl groups being preferred. Preferably, the aromatic ring of such aralkyl groups is substituted by a hydroxyl group. Such groups may be represented by the formula

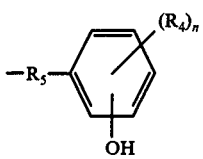

wherein $R_4$, $R_5$ and $n$ are as described above. Preferably the hydroxyl group is in the 4-position and alkyl groups are in both ortho-positions relative to the hydroxyl group. Preferably at least one, more preferably both, alkyl groups are tertiaryalkyl groups e.g. tertiarybutyl groups.

(d) A group which contains at least one heterocyclic ring and is bound directly to the urethane group by means of an aliphatic carbon atom of the group i.e. heterocyclic alkyl groups e.g. thenyl groups.

Suitably the $R_1$ group, of the compound of general formula I, is an alkylene group e.g. a $C_3$ to $C_{10}$ alkylene, e.g. hexamethylene, group, or a group which is bound directly to both the urethane and urea groups by carbon atoms of the same or different aromatic rings such as a phenylene, alkyphenylene, naphthalene, alknaphthalene, biphenylene, alkbiphenylene, a bis(phenylene)alkane or bis(alkylphenylene)alkane group. Preferably, $R_1$ is an alkphenylene group e.g. a tolylene group such as a 1,4 or 1,6-tolylene group or an alkylene group e.g. a hexamethylene group.

Suitably the $R_2$ group of the compound of general formula I, is an alkyl group e.g. a $C_1$ and to $C_{12}$ alkyl group or an aryl, alkaryl or aralkyl group. Suitably, $R_2$ is a phenyl group which is optionally substituted by an alkyl amino group, e.g. a $C_{1-6}$ alkylamino group; preferably the alkyl group is a secondary alkyl group such as a secondary butyl group. Preferably $R_2$ is an alkaryl group comprising from 1 to 3 alkyl groups such as $C_{1-20}$ alkyl groups; preferably only one alkyl group is present which is in the para-position relative to the urea group; suitably the alkyl group is a tertiary alkyl group such as a $C_4$ to $C_{12}$ tertiaryalkyl group. Specific examples of $R_2$ groups include 4-secondarybutylaminophenyl and 4-tertiaryoctylphenyl groups.

Suitably the $R_3$ group, of the compound of general formula I is H, an alkaryl group as described for $R_2$ or a $C_1$-$C_{12}$ alkyl group e.g. a secondary or tertiary alkyl group. Specific examples of $R_3$ groups include secondarybutyl and 4-tertiaryoctylphenyl groups.

The novel compounds of the present invention may be prepared by any convenient process. Suitably they are prepared by either (a) reacting a compound of formula

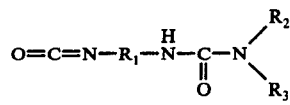

with a compound of formula

R—OH      IV wherein R, $R_1$, $R_2$ and $R_3$ are as hereinbefore described, or (b) reacting a compound of formula

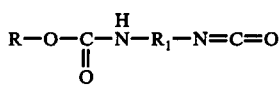

with a compound of formula

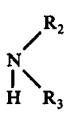

wherein R, $R_1$, $R_2$ and $R_3$ are as hereinbefore described.

The compounds of formula IV are the hydroxyl compounds of the R groups which are described above. The compounds may contain one or more hydroxyl groups which may be aliphatic and or aromatic hydroxyl groups. Examples of compounds having one aliphatic hydroxyl groups are alkanols e.g. dodecanol, thenyl alcohol and 2-methylol pyrrole. Examples of compounds having one aromatic hydroxyl group are phenol, 4-chlorophenol and 2,4-dimethyl-6-tertiarybutyl-phenol. Examples of compounds having two aromatic hydroxyl groups are bisphenols such as bis(2-hydroxy-3-tertiarybutyl-5-methylphenyl)methane. diphenylol propane and diphenylol methane. An example of a compound having an aliphatic and an aromatic hydroxyl group is 3,5-di-tertiarybutyl-4-hydroxybenzyl alcohol.

Suitably the reaction between the compounds of formula III and IV takes place by refluxing a solution of the compounds, suitably the presence of a catalyst e.g. di-n-butyltin-diacetate. Suitable solvents include halohydrocarbons e.g. chloroform or hydrocarbons e.g. toluene and hexane. Preferably approximately equal molar amounts of the compounds are used. The product may be purified by re-crystallization.

The compounds of formula VI are the amines of the $R_2$ and $R_3$ groups which are described above. The compounds may be monoamines or diamines. The amine groups may be primary or secondary-amino groups. An example of a monoamine is 4,4'-di-tertiaryoctyldiphenylamine. An example of a diamine is N,N'-di-isobutylphenylene-1,4-diamine.

Suitably the reaction between the compounds of formulae V and VI takes place under similar conditions as are discussed above for the reaction between the compounds of formulae III and IV.

The compound of formula III may be prepared by reacting a compound of formula

with a compound of formula VI, wherein $R_1$ is as hereinbefore described. The compounds of formula VII are the di-isocyanates of the $R_1$ group which is described above. Examples of suitable di-isocyanates are 2,4-toluene di-isocyanate, 2,6-toluene di-isocyanate and mixtures, e.g. 80:20 mixtures, thereof, 4,4-methylene diphenyl diisocyanate and -1,6-hexamethylene diisocyanate. The reaction is preferably carried out in a solvent such as a halohydrocarbon, e.g. chloroform, or hydrocarbon solvent and at ambient temperature. The amount of reactants is such that only one isocyanate group reacts with the amine. Suitably a molar excess, e.g. a from 2 to 5 molar excess of di-isocyanate is used when the amine is a monoamine. After the reaction, the excess reactant is removed from the product and the product may be purified by re-crystallization before it is reacted with a compound of formula IV.

The compound of formula V may be prepared by reacting a compound of formula VII with a compound of formula IV. The reaction is preferably carried out in a solvent such as a halohydrocarbon e.g. chloroform, or a hydrocarbon solvent and at ambient or a higher temperature. The amount of reactants is such that only one isocyanate group reacts with the hydroxyl compound. Suitably a molar excess, e.g. a 2 to 5 molar excess, of di-isocyanate is used if the hydroxyl compound, reacts under the above reaction conditions, as a monofunctional compound and a molar deficiency of di-isocyanate, e.g. a from 2 to 5 molar excess of hydroxyl compound, is used if the hydroxyl compound reacts, under the above reaction conditions, as a difunctional compound. After the reaction, the excess reactant is removed from the product and the product may be purified by re-crystallization before it is reacted with a compound of formula VI.

The organic compositions of the present invention may comprise from 0.01 to 10%wt of the anti-oxidant, with from 0.1 to 2.0%wt being preferred.

Insofar as the organic material is an oil, the composition may contain other additives such as anti-corrosion agents, additives to improve the viscosity and viscosity-temperature characteristics, ash or ash-less dispersants, pour-point depressants, metal passivators, extreme pressume and antiwear additives. If desired, in addition to the present anti-oxidants, the oil composition may incorporate other compounds having an anti-oxidant action.

The invention will now be illustrated by reference to the following examples.

EXAMPLE 1

(a) Toluene di-isocyanate (552 g, 3.0 mol 80% 2,4, 20% 2,6) and 4,4'-di-tertiaryoctyldiphenylamine (393 g, 1.0 mol) were dissolved in chloroform (1 liter). The solution was stirred (2 hours) and allowed to stand overnight (about 16 hours). The chloroform was stripped off (about 16 mm Hg, 50° C) until precipitation commenced. The residue was dissolved in boiling n-heptane (3 liter) and allowed to stand at room temperature until the product crystallized. The product was then filtered and re-crystallized from n-heptane. The product (yield 60%, m.p. 134°–135° C) had the structure

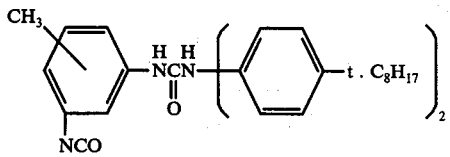

The methyl group may be in the para-position relative to the urea group or in the ortho-position relative to both the urea and the isocyanate groups, with the former position predominating.

(b) The product prepared under (a) (282.5 g, 0.5mol) and 3,5-di-tertiarybutyl-4-hydroxybenzyl alcohol (118 g, 0.5 mol) were dissolved in chloroform (700 ml) and di-n-butyltin-diacetate (0.19 g) added to the solution. The mixture was refluxed (4 hours) and the infra-red absorption band monitored until the isocyanate band (2280 cm$^{-1}$) disappeared. The chloroform was stripped off (about 16 mmHg, 60° C) and the residue dissolved in boiling n-heptane (2 liter) which was allowed to stand at room temperature until the product crystallized (powder form). The product (yield 85%, m.p. 147°–150° C) had the structure

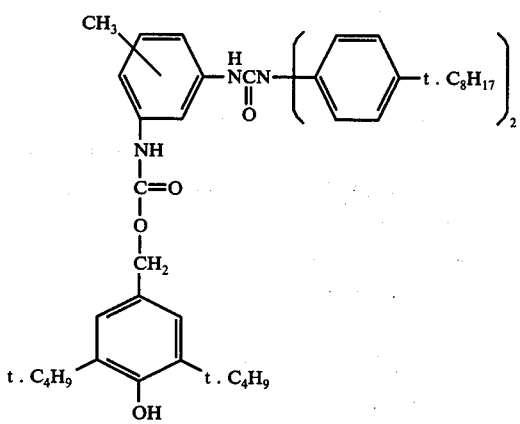

The methyl group may be in the para-position relative to the urea group or in the ortho-position relative to both the urea and the urethane groups, with the former position predominating.

Elemental analysis results were: Found: C-78%, H-10%, N-5%. Calculated: C-77.4%, H-9.4%, N-5.2%.

Infra-red absorbtion bands for the product in $CS_2$ solution were found at

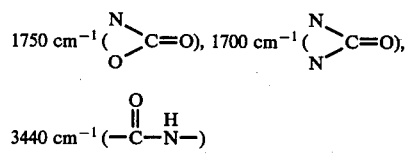

and 3360 cm$^{-1}$ (-Ar-OH).

The proton magnetic resonance spectrum was in agreement with the above structure.

EXAMPLE 2

Example 1 was repeated using, as di-isocyanate, pure toluene-2,4-diisocyanate. A product was obtained having a similar structure to that described under Example 1(b) except that the methyl group is only in the para-position relative to the urea group. The product had similar properties to the product prepared under Example 1(b).

EXAMPLES 3 to 8

Example 1(b) was repeated using, as hydroxyl compounds,
(I) 2,4-dimethyl-6-tertiarybutylphenol (Example 3);
(II) dodecanol (Example 4);

(III) 4-chlorophenol (Example 5);
(IV) bis(2-hydroxy-3-tertiarybutyl-5-methyl-phenyl)methane. (Example 6).
(V) diphenylol propane (Example 7); and
(VI) thenyl alcohol (Example 8).

The products had the structures

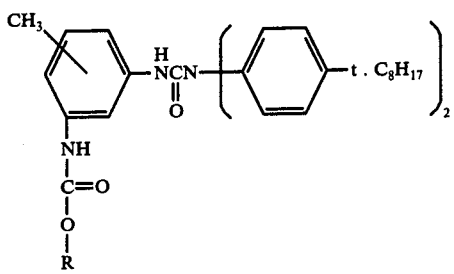

The methyl group may be in the para-position relative to the urea group or in the ortho-position relative to both the urea and urethane groups, with the former position predominating.

The R group of the product of Example 3 (yield 70%, m.p. 176°–179° C) was

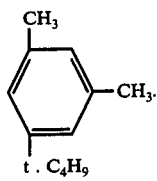

The elemental analysis results were: Found: C-78%, H-9.3%, N-5.6% Calculated: C-78.9%, H-9.0%, N-6.3% Infra-red absorbtion bands for this product in $CS_2$ solution were found at 1750 cm$^{-1}$, 1700 cm$^{-1}$ and 3440 cm$^{-1}$.

The R group of the product of Example 4 (yield 33%, m.p. 152°–166° C) was —$C_{12}H_{25}$. Infra-red absorbtion bands for the product in $CS_2$ solution were found at 1750 cm$^{-1}$, 1700 cm$^{-1}$ and 3420 cm$^{-1}$.

The R group of the product of Example 5 (yield 55%, m.p. 126°–128.5° C) was

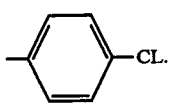

The elemental analysis results were: Found: C-68%, H-8.6%, N-6%, Cl-44% Calculated: C-74.2%, H-7.8%, N-6%, Cl-5.1%

The R group of the product of Example 6 (yield 21%, m.p. 196°–197° C) was

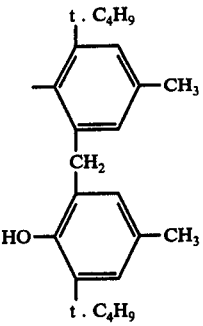

The elemental analysis results were: Found: C-78%, H-10%, N-5%. Calculated: C-79.5%, H-8.9%, N-4.6%. Infra-red absorbtion bands in $CS_2^2$ solution were found at 1750 cm$^{-1}$, 1700 cm$^{-1}$ and 3450 cm$^{-1}$.

The R group of the product of Example 7 (yield 18%, m.p. 106°–120° C) was

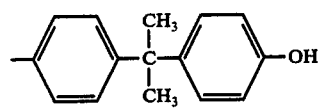

Infra-red absorbtion bands for this product in $CS_2$ solution were found at 1690 cm$^{-1}$, 1760 cm$^{-1}$, 3450 cm$^{-1}$ and 3640 cm$^{-1}$.

The R group of the product of Example 8 (yield 25%) was

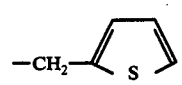

The elemental analysis results were: Found: C-72.5%, H-8.5%, N-6%, S-5% Calculated: C-74%, H-8%, N-6%, S-5%. Infra-red absorbtion bands for this product in $CS_2$ solution were found at 1700 cm$^{-1}$, 1740 cm$^{-1}$ and 3440 cm$^{-1}$.

EXAMPLE 9

(a) Example 1(a) was repeated using, instead of the amine, 3,5-di-tertiarybutyl-4-hydroxybenzyl alcohol. The product obtained had the structure

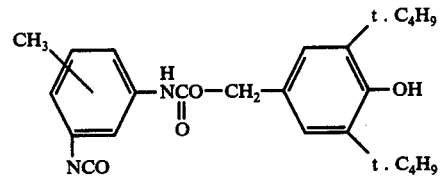

The methyl group may be in the para-position relative to the urethane group or in the ortho-position relative to both the urethane and isocyanate groups, with the former position predominating.

(b) Example 1(b) was repeated using the product prepared under (a) and, instead of the hydroxyl compound, N,N'-di-isobutyl phenylene -1,4-diamine. The product (yield 40%, m.p. 130.5°–151.5° C) had the structure

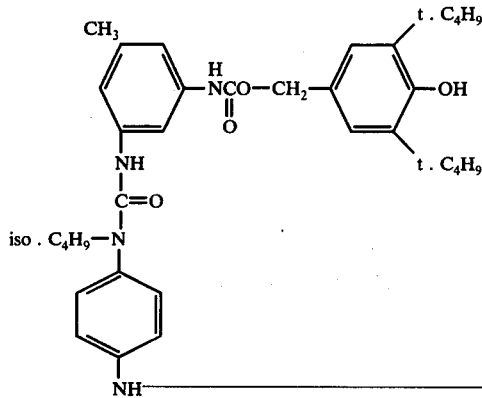

The methyl group may be in the para-position relative to the urethane group or in the ortho-position relative to both the urea and urethane groups, with the former predominating. Elemental analysis results were: Found: C-66%, H-8.8%, N-8.9%. Calculated: C-72.4%, H-8.6%, N-8.9%.

Infra-red absorbtion bands for the product in $CS_2$ solution were found at 1740 $cm^{-1}$, 1680 $cm^{-1}$, 3450 $cm^{-1}$ and 3650 $cm^{-1}$.

EXAMPLE 10

Example 9 was repeated using hexamethylene di-isocyanate instead of toluene di-isocyanate. The final product (yield 32%) had the structure

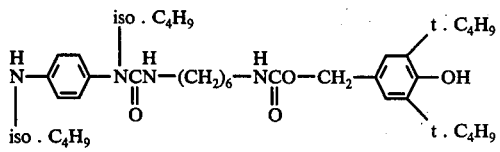

Infra-red absorbtion bands for the products in $CS_2$ solution were found at 1670 $cm^{-1}$, 1730 $cm^{-1}$, 3450 $cm^{-1}$ and 3660 $cm^{-1}$.

EXAMPLES 11 to 16

Six ash-less lubricating oil compositions were prepared by blending the components specified in Table I. The compositions were tested in the air oxidation test (AOT) which comprises passing air (15 liter/hour) through the lubricating oil composition (30g) at 160° C having immersed therein a copper plate and a lead plate (both 9 cm × 1.2 cm). The time taken for 5 ml/g and 10 ml/g of oxygen to be taken up (induction periods) was noted. The change in kinematic viscosity after 168 hours at 210° F was determined as well as the weight losses of the plates after 5 and 168 hours. The results are given in Table II.

TABLE I

| COMPONENTS | Example 11 | Example 12 | Example 13 | Example 14 | Example 15 | Example 16 |
|---|---|---|---|---|---|---|
| Qatar Marine 110 S (HVI oil) | balance | balance | balance | — | — | — |
| Hydrogenated Basrah Deasphalted oil VHVI oil | — | — | — | balance | balance | balance |
| Additive of example 1 (b) | — | 1.0 | 0.5 | — | 1.0 | 0.5 |
| 4,4'-methylene-bis (2,6-ditertiarybutylphenol)* | 0.53 | — | — | 0.53 | — | — |
| Succinimide-type dispersant | 2 | 2 | 2 | 2 | 2 | 2 |
| Hydrogenated benzotriazole (metal passivator) | 0.05 | 0.05 | 0.05 | 0.05 | 0.05 | 0.05 |

*Commercial anti-oxidant

TABLE II

| Example | Induction period (hours) | | Viscosity change after 168 hours (%) (210° F) | Weight loss (mg) | | | |
|---|---|---|---|---|---|---|---|
| | 5 ml/g | 10 ml/g | | 5 hrs. | | 168 hrs. | |
| | | | | Cu | Pb | Cu | Pb |
| 11 | 24.5 | 38 | 112 | 1.3 | 33.7 | 2.0 | 1520 |
| 12 | 46 | 82 | 27.8 | 0.1 | 4.9 | 1.5 | 566 |
| 13 | 35 | 68 | 29.4 | 0.5 | 11.4 | 1.5 | 658 |
| 14 | 36 | 40 | solid | 0.5 | 2.3 | 1.2 | 4071 |
| 15 | 144 | >168 | 11.5 | 0.5 | 1.7 | 1.5 | 179 |
| 16 | 108 | 113 | 77.5 | 0.2 | 3.3 | 0.8 | 1883 |
| 17 | 29 | 53 | 50.4 | 2.0 | 10.7 | 2.7 | 754 |
| 18 | 16 | 34 | 44.1 | 0 | 55.2 | 1.6 | 904 |
| 19 | 20 | 51 | 35.2 | 2 | 35.6 | 1.1 | 757 |
| 20 | 37 | 62.5 | 53.8 | 6 | 10.2 | 1.3 | 895 |

EXAMPLES 17 to 20

Example 13 was repeated using, instead of the additive of Example 1 (b), the additives of Example 6 (Example 17), Example 7 (Example 18), Example 8 (Example 19) and Example 9 (Example 20). The results are also given in Table II.

EXAMPLE 21 and 22

A composition was prepared by adding 0.5%w of the product of Example 1(b) to a HVI motor oil formulation based on a Qatar Marine base oil HVI 60. The composition (Example 21) also contained a styrene/hydrogenated butadiene copolymer as VI improver (3.2%w), a polyisobutylene/maleic anhydride/pentaerythritol adduct as dispersant (2.75%w), a poly(alkyl)acrylate as pour point depressor (0.5%w), a heterocyclic polysul-phide as metal passivator (0.1%w). For comparison a composition (Example 22) was prepared by replacing the product of Example 1(b) in the above formulation by 0.5%w of 4,4'-methylene-bis(2,6-ditertiary butylphenol).

The compositions were tested in the Petter Oil Thickening Test. This test comprises running a Petter W-1 engine for 72 hours under the following conditions:
 oil-sump temperature, 155° C,
 cooling outlet temperature, 160° C,
 speed 1500 rev/min,
 blowby, recycled,
 initial oil change, 1100g,
 total oil make-up, 800g, fuel, leaded,
air/fuel ratio, 14:5:1.

The test is stopped every 12 hours for oil make-up. After each 12 hours of the test all the crankcase oil is drained and a 50g sample taken to determine the change in kinematic viscosity of the oil. Amounts of fresh (160g) and used (to 1100g) oil are then returned to the engine and the surplus used oil is discarded.

The results are given in Table III.

TABLE III

| Test hours | Viscosity increase (%) at 100° F | |
|---|---|---|
| | Example 22 | Example 23 |
| 12 | 8 | 0 |
| 24 | 9 | 3 |
| 36 | 41 | 36 |
| 48 | 105 | 120 |
| 60 | 225 | 390 |
| 72 | 600 | 3200 |

EXAMPLES 23 to 26

Composition were prepared by blending the following ingredients

| | |
|---|---|
| Qatar Marine base oil (HVI 60) | balance |
| Styrene/hydrogenated butadiene copolymer (VI improver) | 3.3 %w |
| Poly(alkyl)acrylate (pour-point depressor) | 0.5 %w |
| Heterocyclic polysulphide(metal passivator) | 0.1 %w |
| polyisobutylene/maleic anhydride/penta-erythritol (dispersant) | 2.75 %w |
| Anti-oxidant | 0.5 %w |

The anti-oxidants used were the product prepared by example 1(b) (Example 23) and 4,4'-methylene-bis(2,6-tertiary butylphenol) (Example 24).

Further compositions were prepared by blending the following ingredients.

| | |
|---|---|
| A VHVI oil (viscosity 9cS) | balance |
| A styrene/hydrogenated isoprene copolymer (VI improver) | 2.75 %w |
| Polyisobutylene/maleic anhydride/pentaerythritol (dispersant) | 2.75 %w(a.m.) |
| A poly(alkyl)acrylate (pour-point depressor) | 0.5 %w |
| Heterocyclic polysulphide (metal-depassivator) | 0.1 %w |
| Antioxidant | 0.5 %w |

The antioxidants used were the product prepared under Example 1(b) (Example 25) and 4,4'-methylene-bis(2,6-di-tertiarybutylphenol) (Example 26).

The compositions were tested in the Petter W-I bearing corrosion test (IP176/69) the results are given in Table IV.

TABLE IV

| Composition | Petter W-1 bearing weight loss, mg | | |
|---|---|---|---|
| | 36 hours | 48 hours | 60 hours |
| 23 | 1.5 | 33.4 | 157.8 |
| 24 | 0.8 | 95.7 | 246.6 |
| 25 | 15 | 49 | — |
| 26 | 15 | 174 | — |

EXAMPLE 27

An ash-less lubricating oil composition were prepared by replacing the anti-oxidant of Example 21 with the anti-oxidant of Example 10 (Example 27).

The AOT test (induction period and weight loss after 5 h) was carried out on the composition and the results are given in Table III. For comparison the results obtained on the composition of Example 22 are also included.

TABLE V

| Example | Induction period (hours) | | Weight loss (mg) | |
|---|---|---|---|---|
| | 5 ml/g | 10 ml/g | Cu | Pb |
| 27 | 51 | 63.5 | 0.6 | 2.5 |
| 23 | 19 | 22.5 | (−)0.4 | 5.8 |

What is claimed is:

1. A compound of the formula:

$$CH_3 \underset{NH}{\overset{}{\bigcirc}} -N(H) - \underset{O}{\overset{}{C}} - N - (\bigcirc - tC_8H_{17})_2$$

$$\underset{|}{NH}$$
$$C=O$$
$$|$$
$$O$$
$$|$$
$$R$$

wherein R is selected from the group consisting of:

[structure: 3,5-di-substituted phenyl with CH$_3$, CH$_3$, tC$_4$H$_9$]

[structure: p-chlorophenyl —C$_6$H$_4$—Cl]

[structure: tC$_4$H$_9$, CH$_3$ substituted phenyl with CH$_2$ linker to OH, CH$_3$, tC$_4$H$_9$ phenyl]

[structure: 4,4'-isopropylidenediphenol type with CH$_3$, C(CH$_3$)$_2$, OH]

, and

2. A compound as in claim 1 wherein R is

[structure: phenyl with CH$_3$, CH$_3$, tC$_4$H$_9$]

3. A compound as in claim 1 wherein R is

[structure: —C$_6$H$_4$—Cl]

4. A compound as in claim 1 wherein R is

5. A compound as in claim 1 wherein R is
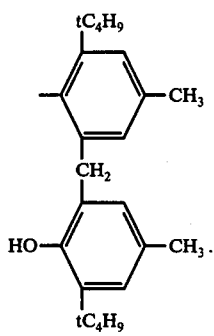
6. A compound as in claim 1 wherein R is
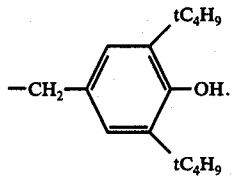
7. A composition comprising a major proportion of a lubricating oil and an oxidation stabilizing amount of a compound as in claim 1.
8. The composition of claim 7 wherein the amount of the oxidation stabilizer compound comprises from 0.01 to 10% by weight.
* * * * *

UNITED STATES PATENT OFFICE
CERTIFICATE OF CORRECTION

PATENT NO. : 4,102,797
DATED : July 25, 1978
INVENTOR(S) : HENDRIK SCHADENBERG

It is certified that error appears in the above-identified patent and that said Letters Patent are hereby corrected as shown below:

At column 12, line 44, after the word "and" insert

-- 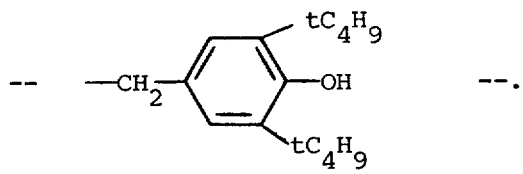 --.

Signed and Sealed this

Sixteenth Day of January 1979

[SEAL]

Attest:

RUTH C. MASON
Attesting Officer

DONALD W. BANNER
Commissioner of Patents and Trademarks